United States Patent
Baxter et al.

[11] Patent Number: 6,063,786
[45] Date of Patent: May 16, 2000

[54] HETEROCYCLIC COMPOUNDS HAVING MMP AND TNF INHIBITORY ACTIVITY

[75] Inventors: Andrew Douglas Baxter; David Alan Owen; John Gary Montana, all of Cambridge, United Kingdom

[73] Assignee: Darwin Discovery, Ltd., United Kingdom

[21] Appl. No.: 09/190,546

[22] Filed: Nov. 12, 1998

Related U.S. Application Data

[60] Provisional application No. 60/068,835, Dec. 24, 1997.

[30] Foreign Application Priority Data

Nov. 12, 1997 [GB] United Kingdom .................. 9723905

[51] Int. Cl.⁷ ...................... A61K 31/513; C07D 239/22
[52] U.S. Cl. ........................... 514/272; 544/231; 544/298
[58] Field of Search ............................ 514/272; 544/298, 544/231

[56] References Cited

U.S. PATENT DOCUMENTS

| | | | |
|---|---|---|---|
| 5,750,704 | 5/1998 | Shiokawa et al. ....................... | 544/298 |
| 5,847,153 | 12/1998 | Warpehoski et al. ................. | 548/319.5 |
| 5,872,152 | 12/1998 | Brown et al. ........................... | 514/575 |

FOREIGN PATENT DOCUMENTS 0234830  9/1987  European Pat. Off. .

OTHER PUBLICATIONS

Wine et al. Metalloproteinase inhibitors . . . Surgery 124, 464–470, 1998.

Hattori et al. Metalloproteinase inhibitors . . . Blood 90, 542–548, 1997.

Houghten et al. Bicyclic Guanidino Ketones, J. Org. Chem. 44, 4536–4543, 1979.

Fukada et al. Synthesis of . . . Synthesis 484–486, 1986.

Birkedal–Hansen et al. Matrix Metalloproteinases: A Review. Cricical Reviews in Oral Biology & Medicine 4(2) 197–250, 1993.

Bodanszky et al. The Practice of Peptide Synthesis. 138–143, 1994.

*Primary Examiner*—Richard L. Raymond
*Assistant Examiner*—Venkataraman Balasubramanian
*Attorney, Agent, or Firm*—Saliwanchik, Lloyd & Saliwanchik

[57] ABSTRACT

Compounds of formula (I)

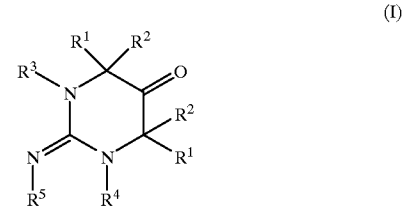

are useful as therapeutic agents, by virtue of having MMP and TNF inhibitory activity.

13 Claims, No Drawings

HETEROCYCLIC COMPOUNDS HAVING MMP AND TNF INHIBITORY ACTIVITY

CROSS-REFERENCE TO A RELATED APPLICATION

This application claims the benefit of the filing dates of U.S. Provisional Application Serial No. 60/068,835 filed Dec. 24, 1997.

FIELD OF THE INVENTION

This invention relates to heterocycles, and to their use in medicine.

BACKGROUND TO THE INVENTION

Metalloproteinases, including matrix metalloproteinases (MMPs), (human fibroblast) collagenase, gelatinase and TNF convertase (TACE), and their modes of action, and also inhibitors thereof and their clinical effects, are described in WO-A-9611209, WO-A-9712902 and WO-A-9719075, the contents of which are incorporated herein by reference. MMP inhibitors may also be useful in the inhibition of other mammalian metalloproteinases such as the adamalysin family (or ADAMs) whose members include TNF convertase (TACE) and ADAM-10, which can cause the release of TNF α from cells, and others, which have been demonstrated to be expressed by human articular cartilage cells and also involved in the destruction of myelin basic protein, a phenomenon associated with multiple sclerosis.

Compounds which have the property of inhibiting the action of metalloproteinases involved in connective tissue breakdown, such as collagenases, stromelysins and gelatinases, have been shown to inhibit the release of TNF both in vitro and in vivo. See Gearing et al (1994), Nature 370:555–557; McGeehan et al (1994), Nature 370:558–561; GB-A-2268934; and WO-A-9320047. All of these reported inhibitors contain a hydroxamic acid zinc-binding group, as do the imidazole-substituted compounds disclosed in WO-A-9523790. Other compounds that inhibit MMP and/or TNF are described in WO-A-9513289, WO-A-9611209, WO-A-96035687, WO-A-96035711, WO-A-96035712 and WO-A-96035714.

SUMMARY OF THE INVENTION

The invention encompasses compounds which are useful inhibitors of matrix metalloproteinases and/or TNF α-mediated diseases, including degenerative diseases and certain cancers. Novel compounds according to the invention are of the general type represented by formula (I):

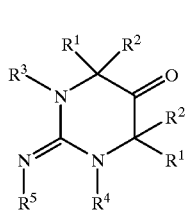

(I)

wherein each $R^1$ is independently H or a group (optionally substituted with $R^{10}$) selected from $C_{1-6}$ alkyl, $C_{2-6}$ alkenyl, aryl, $C_{1-6}$ alkyl-aryl, heteroaryl, $C_{1-6}$ alkyl-heteroaryl, heterocycloalkyl, $C_{1-6}$ alkyl-heterocycloalkyl, cycloalkyl and $C_{1-6}$ alkyl-cycloalkyl;

each $R^2$ is independently H or $C_{1-6}$ alkyl;

or either or each of $CR^1R^2$ may alternatively represent cycloalkyl or heterocycloalkyl, optionally substituted with $R^{10}$ or a group (optionally substituted with $R^{10}$) selected from $C_{1-6}$ alkyl, aryl, heteroaryl, $C_{1-6}$ alkyl-heteroaryl and $C_{1-6}$ alkyl-aryl, and each instance of $CR^1R^2$ may be the same or different;

$R^3$ is $S(O)_{1-2}R^9$, $SO_2N(R^7)_2$, $CO_2R^7$, $CON(R^7)_2$, $COR^7$, $CONR^{11}OR^7$ or $R^5$; $R^4$ is H or $R^5$;

$R^5$ is $C_{1-6}$ alkyl-aryl, $C_{1-6}$ alkyl, $C_{2-6}$ alkenyl, cycloalkyl, $C_{1-6}$ alkyl-cyloalkyl, cycloalkenyl, $C_{1-6}$ alkyl-cycloalkenyl, heterocycloalkenyl, $C_{1-6}$ alkyl-heterocycloalkenyl, $C_{1-6}$ alkyl-heteroaryl, heterocycloalkyl, $C_{1-6}$ alkyl-heterocycloalkyl, aryl or heteroaryl, any of which groups is optionally substituted by a substituent selected from $R^6$, $C_{1-6}$ alkyl-$R^6$, aryl (optionally substituted with $R^6$), $C_{1-6}$ alkyl-aryl (optionally substituted with $R^6$), $C_{1-6}$ alkyl-heteroaryl (optionally substituted with $R^6$), heteroaryl (optionally substituted with $R^6$), cycloalkyl (optionally substituted with $R^6$), heterocycloalkyl (optionally substituted with $R^6$), and each instance of $R^5$ may be the same or different;

$R^6$ is halogen, CN, $NO_2$, $N(R^7)_2$, $OR^7$, $NR^7R^8$, $S(O)_{1-2}R^9$, $SO_2N(R^7)_2$, $CO_2R^{11}$, $CON(R^7)_2$, $COR^7$, $CONR^{11}OR^7$, or $C_{1-6}$ alkyl;

$R^7$ is H or a group selected from $C_{1-6}$ alkyl, aryl, $C_{1-6}$ alkyl-aryl, heteroaryl, $C_{1-6}$ alkyl-heteroaryl, cycloalkyl, $C_{1-6}$ alkyl-cycloalkyl, heterocycloalkyl and $C_{1-6}$ alkyl-heterocycloalkyl, wherein said group is optionally substituted with $R^9$, $COR^9$, $SO_{0-2}R^9$, $CO_2R^9$, $OR^9$, SH, OH, $SCOR^9$, $CONR^{11}R^9$, $NR^{11}R^9$, halogen, CN, $SO_2NR^{11}R^9$ or $NO_2$, and for each case of $N(R^7)_2$ the $R^7$ groups are the same or different or $N(R^7)_2$ is heterocycloalkyl optionally substituted with $R^9$, $COR^9$, $SO_{0-2}R^9$, $CO_2R^9$, $OR^9$, SH, OH, $SCOR^9$, $CONR^{11}R^9$, $NR^{11}R^9$, CN or $SO_2NR^{11}R^9$;

$R^8$ is $COR^7$, $CON(R^7)_2$, $CO_2R^9$ or $SO_2R^9$;

$R^9$ is $C_{1-6}$ alkyl, aryl, $C_{1-6}$ alkyl-aryl, heteroaryl or $C_{1-6}$ alkyl-heteroaryl; and $R^{10}$ is $OR^7$, $COR^7$, $CO_2R^{11}$, $CON(R^7)_2$, $NR^7R^8$, $S(O)_{0-2}R^9$, $SO_2N(R^7)_2$, halogen, CN, $NO_2$ or cycloimidyl (optionally substituted with $R^{11}$)

$R^{11}$ is H or $C_{1-6}$ alkyl;

and the salts, solvates, hydrates, N-oxides, protected amino and protected carboxy derivatives thereof.

Combinations of substituents and/or variables are only permissible if such combinations result in staple compounds.

DESCRIPTION OF THE INVENTION

Preferred compounds of the invention are those wherein any one or more of the following apply:

$R^1$ is optionally substituted $C_{1-6}$ alkyl, $C_{1-6}$ alkyl-aryl, $C_{1-6}$ alkyl-heteroaryl or $C_{1-6}$ alkyl-heterocycloalkyl;

$R^1$ at the position adjacent to N—$R^4$ is H or $C_{1-6}$ alkyl;

$R^3$ is $CO_2R^7$, $CON(R^7)_2$, $COR^7$, or $CONR^{11}OR^7$;

$R^4$ is optionally substituted $C_{1-6}$ alkyl-aryl, $C_{1-6}$ alkyl, $C_{1-6}$ alkyl-cycloalkyl, $C_{1-6}$ alkyl-cycloalkenyl, $C_{1-6}$ alkyl-heteroaryl, heterocycloalkyl, $C_{1-6}$ alkyl-heterocycloalkyl, aryl or heteroaryl; and $R^5$ is optionally substituted $C_{1-6}$ alkyl-aryl, $C_{1-6}$ alkyl, $C_{2-6}$ alkenyl, $C_{1-6}$ alkyl-heteroaryl, aryl or heteroaryl.

The compounds of the examples are particularly preferred.

It will be appreciated that the compounds according to the invention can contain one or more asymmetrically substituted carbon and sulfur atoms. The presence of one or more of these asymmetric centres in a compound of formula (I) can give rise to stereoisomers, and in each case the invention is to be understood to extend to all such stereoisomers, including enantiomers and diastereomers, and mixtures including racemic mixtures thereof.

As used in this specification, alone or in combination, the term "$C_{1-6}$ alkyl" refers to straight or branched chain alkyl moiety having from one to six carbon atoms, including for example, methyl, ethyl, propyl, isopropyl, butyl, tert-butyl, pentyl, hexyl and the like.

The term "$C_{2-6}$ alkenyl" refers to a straight or branched chain alkyl moiety having two to six carbon atoms and having in addition one double bond, of either E or Z stereochemistry where applicable. This term would include for example, vinyl, 1-propenyl, 1- and 2-butenyl, 2-methyl-2-propenyl etc.

The term "cycloalkyl" refers to a saturated alicyclic moiety having from three to six carbon atoms and which may be optionally benzofused at any available position. This term includes, for example, cyclopropyl, cyclobutyl, cyclopentyl, cyclohexyl, indanyl, tetrahydronaphthyl and the like.

The term "heterocycloalkyl" refers to a saturated heterocyclic moiety having from three to six carbon atoms and one or more heteroatom from the group, N, O, S (or oxidised versions thereof) which may be optionally benzofused at any available position. This term includes, for example, azetidinyl, pyrrolidinyl, tetrahydrofuranyl, piperidinyl, indolinyl, tetrahydroquinolinyl and the like.

The term "cycloalkenyl" refers to an alicyclic moiety having from three to six carbon atoms and having in addition one double bond. This term would include for example cyclopentenyl or cyclohexenyl.

The term "heterocycloalkenyl" refers to an alicyclic moiety having from three to six carbon atoms and one or more heteroatoms from the group N, O, S (or oxidised versions thereof) and having in addition one double bond. This term includes, for example, dihydropyranyl.

The term "aryl" refers to an aromatic carbocyclic radical having a single ring or two condensed rings. This term includes, for example phenyl or naphthyl.

The term "heteroaryl" refers to aromatic ring systems of five to ten atoms of which at least one atom is selected from O, N and S, and includes for example furanyl, thiophenyl, pyridyl, indolyl, quinolyl and the like.

The term "cycloimidyl" refers to a saturated ring of five to ten atoms containing the atom sequence —C(=O)NC(=O)—. The ring may be optionally benzofused at any available position. Examples include succinimidoyl, phthalimidoyl and hydantoinyl.

The term "benzofused" refers to the addition of a benzene ring sharing a common bond with the defined ring system.

The term "optionally substituted" means optionally substituted with one or more of the groups specified, at any available position or positions.

The term "halogen" means fluorine, chlorine, bromine or iodine.

The terms "protected amino" and "protected carboxy" mean amino and carboxy groups which can be protected in a manner familiar to those skilled in the art. For example, an amino group can be protected by a benzyloxycarbonyl, tert-butoxycarbonyl, acetyl or like group, or may be in the form of a phthalimido or like group. A carboxyl group can be protected in the form of a readily-cleavable ester such as the methyl, ethyl, benzyl or tert-butyl ester.

Salts of compounds of formula (I) include pharmaceutically-acceptable salts, for example acid addition salts derived from inorganic or organic acids, such as hydrochlorides, hydrobromides, p-toluenesulphonates, phosphates, sulphates, perchlorates, acetates, trifluoroacetates, propionates, citrates, malonates, succinates, lactates, oxalates, tartrates and benzoates.

Salts may also be formed with bases. Such salts include salts derived from inorganic and organic bases, for example alkali metal salts such as magnesium or calcium salts, and organic amine salts such as morpholine, piperidine, dimethylamine or diethylamine salts.

When the "protected carboxy" group in compounds of the invention is an esterified carboxyl group, it may be a metabolically-labile ester of formula $CO_2R^{12}$ where $R^{12}$ may be an ethyl, benzyl, phenethyl, phenylpropyl, α or β-naphthyl, 2,4-dimethylphenyl, 4-tert-butylphenyl, 2,2,2-trifluoroethyl, 1-(benzyloxy)benzyl, 1-(benzyloxy)ethyl, 2-methyl-1-propionyloxypropyl, 2,4,6-trimethylbenzyloxymethyl or pivaloylmethyl group.

Compounds of the general formula (I) may be prepared by any suitable method known in the art and/or by the following processes.

It will be appreciated that, where a particular stereoisomer of formula (I) is required, the synthetic processes described herein may be used with the appropriate homochiral starting material and/or isomers may be resolved from mixtures using conventional separation techniques (e.g. HPLC).

The compounds according to the invention may be prepared by the following process. In the description and formulae below the groups $R^1$, $R^2$, $R^3$, $R^4$, $R^5$, $R^6$, $R^7$, $R^8$, $R^9$, $R^{10}$, $R^{11}$ and $R^{12}$ are as defined above, except where otherwise indicated. It will be appreciated that functional groups, such as amino, hydroxyl or carboxyl groups, present in the various compounds described below, and which it is desired to retain, may need to be in protected form before any reaction is initiated. In such instances, removal of the protecting group may be the final step in a particular reaction. Suitable protecting groups for such functionality will be apparent to those skilled in the art. For specific details see Greene et al, "Protective Groups in Organic Synthesis", Wiley Interscience.

A process for preparing compounds of general formula (I) comprises the treatment of an amine of formula $R^3NHCR^1R^2COCR^1R^2NHR^4$ (II) with an isocyanate of formula $R^5NCO$ in an appropriate solvent, e.g. dichloromethane, at an appropriate temperature, e.g. room temperature.

Amines of formula (II) may be prepared by reaction of an amine of formula $R^4NH_2$ (III) with compounds of formula $R^3NHCR^1R^2COCR^1R^2Z$ (IV), where Z represents a suitable leaving group such as a halide or an arylsulfonate. This reaction may be performed in a suitable solvent, e.g. acetonitrile or dimethylformamide, in the presence of an organic base such as triethylamine, or an inorganic base such as potassium carbonate.

Compounds of formula (I) may also be prepared directly from compounds of formula (IV) by sequential reaction with an amine of of formula (III) under appropriate conditions and in situ treatment with an isocyanate $R^5NCO$.

Compounds of formula (IV) where Z is a halogen may be prepared from compounds of formula $R^3NHCR^1R^2COOH$ (V) in a three-step process involving activation of the acid to a compound of formula $R^3NHCR^1R^2COX$ (VI), where COX represents a suitable activated carboxylic acid such as a mixed anhydride, and then treatment with diazoalkane, and then treatment with a source of ionic bromide. Suitable conditions for this process include treatment of the acid (V) with a chloroformate such as isopropyl chloroformate, in the presence of an organic case such as triethylamine in an inert solvent such as tetrahydrofuran, to give an activated compound of formula (VI) where X is $OCOCH(CH_3)_2$, then treatment with diazoalkane in an inert solvent such as ether, at a suitable temperature such as 0° C., then treatment with concentrated hydrobromic acid in acetic acid at a suitable temperature, such as 0° C. to room temperature.

Compounds of formula (IV) where Z is a halogen may be prepared alternatively by halogenation of a compound of formula $R^3NHCR^1R^2COCHR^1R^2$ (VII). Suitable conditions for this reaction include bromine in the presence of a catalytic amount of an organic or inorganic acid in an appropriate solvent. Compounds of formula (VII) may be prepared by reaction of an activated acid of formula (VI), where X is, for example, NMeOMe, with a compound of formula $MCR^1R^2$ (VIII) where M is a metal such as Li or Mg, in an inert solvent such as tetrahydrofuran.

Compounds of formula (II) may be prepared by interconversion of other compounds of formula (II). Thus, for example, a compound (II) where $R^1$ is $C_{1-6}$ alkyl may be prepared from a compound (II) where $R^1$ is H by treatment with strong base, such as lithium di-isopropylamide in an inert solvent such as tetrahydrofuran at an appropriate temperature, such as −78° C. to 0° C., followed by addition of an alkylating agent of formula $ZR^1$ (IX). This procedure may require the temporary protection of an amino group in the compound of formula (II) followed by deprotection. The introduction and removal of an appropriate protecting group is well known to those skilled in the art (e.g. see Greene et al, "Protective Groups in Organic Synthesis", Wiley Interscience).

Many amines of formula (III) or acids or formula (V) or compounds of formula (VIII) and (IX) are commercially available, or may be prepared from compounds available commercially using standard methods known to those skilled in the art.

Compounds of formula (I) may also be prepared by interconversion of other compounds of formula (I). Thus, for example, a compound of formula (I) wherein $R^1$ is a $C_{1-6}$ alkyl group may be prepared by hydrogenation (using palladium on carbon in suitable solvent, such as an alcohol, e.g. ethanol) of a compound of formula (I) wherein $R^1$ is a $C_{2-6}$ alkenyl group.

Any mixtures of final products or intermediates obtained can be separated on the basis of the physico-chemical differences of the constituents, in known manner, into the pure final products or intermediates, for example by chromatography, distillation, fractional crystallization, or by formation of a salt if appropriate or possible under the circumstances.

The compounds according to the invention exhibit in vitro inhibiting activities with respect to the stromelysins, collagenases and gelatinases. Compounds according to the invention may also exhibit in vitro inhibition of membrane shedding events known to be mediated by metalloproteinases, for example, TNF release, TNF receptor shedding, IL-6 receptor shedding, IL-1 receptor shedding, CD23 shedding and L-selectin shedding. The activity and selectivity of the compounds may be determined by use of the appropriate enzyme inhibition test, for example as described in Examples A–M of WO 98/05635, or by the following assay for the inhibition of CD23 shedding.

The potency of compounds of general formula (I) to act as inhibitors of the shedding of CD23 is determined using the following procedure: a 100 $\mu$M solution of the compound being tested, or dilutions thereof, is incubated at 37° C. in an atmosphere of 5% $CO_2$ with RPMI 8866 cells, which shed CD23 spontaneously without stimulation. After 1 h, the cells are removed by centrifugation and the supernatant assayed for levels of sCD23 using an ELISA kit available commercially. The activity in the presence of 0.1 mM inhibitor, or dilutions thereof, is compared to activity in a control devoid of inhibitor and the results reported as that inhibitor concentration effecting 50% inhibition of the shedding of CD23.

This invention also relates to a method of treatment for patients (including man and/or mammalian animals raised in the dairy, meat or fur industries or as pets) suffering from disorders or diseases which can be attributed to MMPs as previously described, and more specifically, a method of treatment involving the administration of the matrix metalloproteinase inhibitors of formula (I) as the active constituents.

Accordingly, the compounds of formula (I) can be used among other things in the treatment of osteoarthritis and rheumatoid arthritis, and in diseases and indications resulting from the over-expression of these matrix metalloproteinases such as found in certain metastatic tumour cell lines.

As mentioned above, compounds of formula (I) are useful in human or veterinary medicine since they are active as inhibitors of TNF and MMPs. Accordingly in another aspect, this invention concerns:

a method of management (by which is meant treatment of prophylaxis) of disease or conditions mediated by TNF and/or MMPs in mammals, in particular in humans, which method comprises administering to the mammal an effective, amount of a compound of formula (I) above, or a pharmaceutically acceptable salt thereof; and a compound of formula (I) for use in human or veterinary medicine, particularly in the management (by which is meant treatment or prophylaxis) of diseases or conditions mediated by TNF and/or MMPs; and the use of a compound of formula (I) in the preparation of an agent for the management (by which is meant treatment or prophylaxis) of diseases or conditions mediated by TNF and/or MMPs.

The disease or conditions referred to above include inflammatory diseases, autoimmune diseases cancer, cardiovascular diseases, diseases involving tissue breakdown such as rheumatoid arthritis, osteoarthritis, osteoporosis, neurodegeneration, Alzheimer's disease, stroke, vasculitis, Crohn's disease, ulcerative colitis, multiple sclerosis, periodontitis, gingivitis and those involving tissue breakdown such as bone resorption, haemorrhage, coagulation, acute phase response, cachexia and anorexia, acute infections, HIV infections, fever, shock states, graft versus host reactions, dermatological conditions, surgical wound healing, psoriasis, atopic dermatitis, epidermolysis bullosa, tumour growth, angiogenesis and invasion by secondary metastases, ophthalmological disease, retinopathy, corneal ulceration, reperfusion injury, migraine, meningitis, asthma, rhinitis, allergic conjunctivitis, eczema, anaphylaxis, restenosis, congestive heart failure, endometriosis, atherosclerosis, endosclerosis and aspirin-independent anti-thrombosis.

Compounds of formula (I) may also be useful in the treatment of pelvic inflammatory disease (PID), age-related macular degeneration and cancer-induced bone resorption. Further, they can be used in the treatment of lung diseases, e.g. selected from cystic fibrosis, adult respiratory distress syndrome (ARDS), emphysema, bronchitis obliterans-organising pneumonia (BOOP), idiopathic pulmonary fibrosis (PIF), diffuse alveolar damage, pulmonary Langerhan's cell granulamatosis, pulmonary lymphangioleiomyomatosis (LAM) and chronic obstructive pulmonary disease (COPD).

For the treatment of rheumatoid arthritis, osteoarthritis, and in diseases and indications resulting from the overexpression of matrix metalloendoproteinases such as found in certain metastatic tumour cell lines or other diseases mediated by the matrix metalloendoproteinases or increased TNF production, the compounds of formula (I) may be administered orally, topically, parenterally, by inhalation spray or rectally in dosage unit formulations containing non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats etc, the compounds of the invention are effective in the treatment of humans.

The pharmaceutical composition containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874, to form osmotic therapeutic tablets for control release.

Formulations for oral use may also be presented as hard gelatin capsules where in the active ingredient is mixed with an inert solid diluent, for example calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate polyvinyl-pyrrolidone, gum tragacanth and gum acacia; dispersing or wetting agents may be a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified, for example sweetening, flavouring and colouring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be in a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc containing the compounds of Formula (I) are employed. For the purposes of this specification, topical application includes mouth washes and gargles.

Dosage levels of the order of from about 0.05 mg to about 140 mg per kilogram of body weight per day are useful in the treatment of the above-indicated conditions (about 2.5 mg to about 7 g per patient per day). For example, inflammation may be effectively treated by the administration of from about 0.01 to 50 mg of the compound per kilogram of body weight per day (about 0.5 mg to about 3.5 g per patient per day).

The amount of active ingredient that may be combined with the carrier materials to produce a single dosage form will vary depending upon the host treated and the particular mode of administration. For example, a formulation intended for the oral administration of humans may vary from about 5 to about 95% of the total composition. Dosage unit forms will generally contain between from about 1 mg to about 500 mg of active ingredient.

It will be understood, however, that the specific dose level for any particular patient will depend upon a variety of factors including the activity of the specific compound employed, the age, body weight, general health, sex, diet time of administration, route of administration, rate of excretion, drug combination and the severity of the particular disease undergoing therapy.

The following Examples illustrate the invention.

In the Examples, the following abbreviations are used:

TNFα Tumour Necrosis Factor α

LPS Lipopolysaccharide

ELISA Enzyme-linked immunosorbent assay

EDC 1-Ethyl-2-dimethylaminopropylcarbodiimide

RT Room Temperature

Rt Retention time

In the following description, HPLC-MS was performed on a Hewlett Packard 1100 LC using a Phenomenex Luna C18, 50×2.1 mm column at 35° C., running a solvent A: solvent B gradient of 95:5 to 35:65 in 4.70 min and to 0:100 in 1.50 min at a flow rate of 0.90 mL/min. Solvent A and solvent B are 95% water:5% acetonitrile 0.1% formic acid and 5% water: 95% acetonitrile 0.1% formic acid respectively. MS spectra were acquired at 1 cone voltage (30V), on a Micromass Quattro (triple quadrupole) instrument.

Intermediate 1

1-Bromo-3S-(tert-butyloxycarbonylamino)-5-methylhexan-2-one

Ethyl chloroformate (1.24 mL) was added to a solution of BOC-Leu (2.31 g) and N-methyl morpholine (1.50 mL) in dry THF (30 mL) at −15° C. The mixture was stirred at that temperature 1 h 30 min, and then the white precipitate was removed by filtration. To the filtrate at 0° C. was added dropwise a solution of diazomethane (nominally 16.6 mmol) in ether (70 mL). The resulting yellow solution was stirred at 0° C. for 1 h, and then allowed to warm to room temperature over 1 h. A mixture of 48% aqueous HBr (10 mL) in glacial acetic acid (10 mL) was then added slowly with efficient stirring, and then the mixture was stirred a further 1 h at room temperature. The reaction was quenched by the careful addition of solid sodium bicarbonate and water (50 mL) to pH 8, and then the solution was extracted with ethyl acetate (4×75 mL). The extracts were combined and washed with saturated brine (25 mL), then dried over MgSO$_4$, filtered and evaporated to give the crude product as a yellow oil. Purification by flash column chromatography over silica gel, eluting with 10% ethyl acetate in hexane, gave the title compound as a pale yellow solid (1.76 g, 57%).
R$_f$ 0.39 (10% EtOAc-hexane)

EXAMPLE 1

3-Benzyl-2-ethylimino-6S-(2-methylprop-1-yl)-5-oxo-tetrahydro-pyrimidine-1-carboxylic Acid tert-Butyl Ester Potassium carbonate (0.19 g) and benzylamine (0.15 mL) were added to a stirred solution of intermediate 1 in dry dimethylformamide at 0° C., and the mixture was stirred 1 h. Ethyl isocyanate (0.11 mL) was then added to the mixture and stirring was continued overnight. The mixture was the partitioned between ethyl acetate (50 mL) and water (30 mL), and the layers were separated. The aqueous layer was extracted with ethyl acetate (40 mL), and the ethyl acetate layers were combined and washed with water (5×20 mL) and brine (20 mL), the dried over MgSO$_4$, filtered and evaporated to give the crude product as viscous yellow oil. This crude product was purified by flash column chromatography on silica gel, eluting with 40–50% ethyl acetate in hexane, to give the title compound as a colourless solid. (0.27 g, 48%).
R$_f$ 0.26 (40% EtOAc-hexane)
MS 388 (MH$^+$)

EXAMPLE 2

2-Cyclohexylimino-6S-(2-methylprop-1-yl)-3-isopropyl-5-oxo-tetrahydropyrimidine-1-carboxylic Acid tert-Butyl Ester To a solution of intermediate 1 in acetonitrile (0.5 mL, 0.1 M) was added at room temperature a solution of isopropylamine (0.5 mL, 0.1 M), a solution of diisopropylethylamine (0.5 mL, 0.17 M) and a solution of cyclohexyl isocyanate (0.5 mL, 0.1 M). The mixture was allowed to stand overnight, then partitioned between ethyl acetate (5 mL) and water (3 mL), and the layers were separated. The organic layer was then dried over MgSO$_4$, filtered and evaporated to give the the title compound (7 mg) as a yellow oil.
HPLC R$_t$ (min) 4.98
MS 393 (MH$^+$)

Similarly prepared were:

EXAMPLE 3

3-(2-Cyclohex-1-enylethyl)-6S-(2-methylprop-1-yl)-5-oxo-2-(1-phenylethylimino)-tetrahydropyrimidine-1-carboxylic Acid tert-Butyl Ester From intermediate 1, 2-cyclohex-1-enylethylamine and 1-phenylethyl isocyanate, as a yellow solid (15 mg).
HPLC R$_t$ (min) 4.81
MS 481 (MH$^+$)

EXAMPLE 4

3-Cyclohexyl-6S-(2-methylprop-1-yl)-5-oxo-2-(1-phenylethylimino)-tetrahydropyrimidine-1-carboxylic Acid tert-Butyl Ester From intermediate 1, cyclohexylamine and 1-phenyl-ethyl isocyanate, as a yellow solid (12 mg).
HPLC R$_t$ (min) 5.61
MS 455 (MH$^+$)

EXAMPLE 5

6S-(2-methylprop-1-yl)-5-oxo-2-(1-phenyl-ethylimino)-3-(3-phenyl-propyl)-tetrahydro-pyrimidine-1-carboxylic Acid tert-Butyl Ester From intermediate 1, 3-phenylpropylamine and 1-phenylethyl isocyanate, as a yellow oil (18 mg).

HPLC R$_t$ (min.) 5.72
MS 491 (MH$^+$)

EXAMPLE 6
3-(2-Cyclohex-1-enylethyl)-2-cyclohexylimino-6S-(2-methylprop-1-yl)-5-oxo-tetrahydro-pyrimidine-1-carboxylic Acid tert-Butyl Ester From intermediate 1, 2-cyclohex-1-enyl-ethylamine and cyclohexyl isocyanate, as a yellow solid (18 mg).
HPLC R$_t$ (min) 6.03
MS 459 (MH$^+$)

EXAMPLE 7
2-Cyclohexylimino-6S-(2-methylprop-1-yl)-5-oxo-3-(2-piperidin-1-yl-ethyl)-tetrahydro-pyrimidine-1-carboxylic Acid tert-Butyl Ester From intermediate 1, 2-piperidin-1-yl-ethylamine and cyclohexyl isocyanate, as a yellow oil (16 mg).
HPLC R$_t$ (min) 2.99
MS 462 (MH$^+$)

EXAMPLE 8
2-Cyclohexylimino-6S-(2-methylprop-1-yl)-5-oxo-3-(3-phenyl-propyl)-tetrahydro-pyrimidine-1-carboxylic Acid tert-Butyl Ester From intermediate 1, 3-phenyl-propylamine and cyclohexylisocyanate, as a yellow oil (9 mg).
HPLC R$_t$ (min) 5.81
MS 469 (MH$^+$)

EXAMPLE 9
3-(2-Cyclohex-1-enyl-ethyl)-6S-(2-methylprop-1-yl)-5-oxo-2-pentylimino-tetrahydro-pyrimidine-1-carboxylic Acid tert-Butyl Ester From intermediate 1, 2-cyclohex-1-enyl-ethylamine and pentyl isocyanate, as a yellow solid (12 mg).
HPLC R$_t$ (min) 5.89
MS 447 (MH$^+$)

EXAMPLE 10
6S-(2-methylprop-1-yl)-5-oxo-2-pentylimino-3-(3-phenyl-propyl)-tetrahydro-pyrimidine-1-carboxylic Acid tert-Butyl Ester From intermediate 1, 3-phenyl-propylamine and pentyl isocyanate, as yellow oil (13 mg).
HPLC R$_t$ (min) 5.73
MS 457 (MH$^+$)

EXAMPLE 11
2-Ethylimino-6S-(2-methylprop-1-yl)-5-oxo-3-(3-phenyl-propyl)-tetrahydro-pyrimidine-1-carboxylic Acid tert-Butyl Ester From intermediate 1, 3-phenyl-propylamine and ethyl isocyanate, as yellow oil (8 mg).
HPLC R$_t$ (min) 4.87
MS 415 (MH$^+$)

EXAMPLE 12
3-(2-Cyclohex-1-enyl-ethyl)-6S-(2-methylprop-1-yl)-2-(1-naphthalen-1-yl-ethylimino)-5-oxo-tetrahydro-pyrimidine-1-carboxylic Acid tert-Butyl Ester From intermediate 1, 2-cyclohex-1-enyl-ethylamine and 1-naphthalen-1-yl-ethyl isocyanate, as a yellow soild (15 mg).
HPLC R$_t$ (min) 6.15
MS 531 (MH$^+$)

EXAMPLE 13
6S-(2-methylprop-1-yl)-2-(1-naphthalen-1-yl-ethylimino)-5-oxo-3-(3-phenyl-propyl)-tetrahydro-pyrimidine-1-carboxylic Acid tert-Butyl Ester From intermediate 1, 3-phenyl-propylamine and 1-naphthalen-1-yl-ethylisocyanate as a yellow solid (11 mg).
HPLC R$_t$ (min) 6.00
MS 541 (MH$^+$)

EXAMPLE 14
2-Allylimino-3-(2-cyclohex-1-enyl-ethyl)-6S-(2methylprop-1-yl)-5-oxo-tetrahydro-pyrimidine-1-carboxylic Acid tert-Butyl Ester From intermediate 1, 2-cyclohex-1-enyl-ethylamine and allyl isocyanate, as a yellow oil (10 mg).
HPLC R$_t$ (min) 5.21
MS 417 (MH$^+$)

EXAMPLE 15
2-Allylimino-6S-(2-methylprop-1-yl)-5-oxo-3-(2-piperidin-1-yl-ethyl)-tetrahydro-pyrimidine-1-carboxylic Acid tert-Butyl Ester From intermediate 1, 2-piperidin-1-yl-ethyl amine and allyl isocyanate, as a yellow oil (12 mg).
HPLC R$_t$ (min) 2.41
MS 420 (MH$^+$)

EXAMPLE 16
2-Allylimino-3-cyclohexyl-6S-(2-methylprop-1-yl)-5-oxo-tetrahydro-pyrimidine-1-carboxylic Acid tert-Butyl Ester From intermediate 1, cyclohexylamine and allyl isocyanate, as a yellow oil (10 mg)
HPLC R$_t$ (min) 4.83
MS 391 (MH$^+$)

EXAMPLE 17
2-Allylimino-6S-(2-methylprop-1-yl)-5-oxo-3-(3-phenyl-propyl)-tetrahydro-pyrimidine-1-carboxylic Acid tert-Butyl Ester From intermediate 1, 3-phenyl-propylamine and allyl isocyanate, as yellow oil (14 mg).
HPLC R$_t$ (min) 5.04
MS 427 (MH$^+$)

What is claimed is:
1. A compound represented by formula (I):

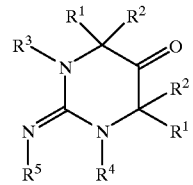

wherein
each $R^1$ is independently H or a substituent (optionally substituted with $R^{10}$) selected from the group consisting of $C_{1-6}$ alkyl, $C_{2-6}$ alkenyl, aryl, $C_{1-6}$ alkyl-aryl, furanyl, thiophenyl, pyridyl, indolyl, quinolyl, $C_{1-6}$ alkyl-heteroaryl, azetidinyl, pyrrolidinyl, tetrahydrofuranyl, piperidinyl, indolinyl, tetrahydroquinolinyl, $C_{1-6}$ alkyl-heterocycloalkyl, cycloalkyl and $C_{1-6}$ alkyl-cycloalkyl;

each $R^2$ is independently H or $C_{1-6}$ alkyl;

or either or each of $R^1R^2$ may alternatively represent cycloalkyl or azetidinyl, pyrrolidinyl, tetrahydrofuranyl, piperidinyl, indolinyl, tetrahydroquinolinyl, optionally substituted with $R^{10}$ or a substituent (optionally substituted with $R^{10}$) selected from the group consisting of $C_{1-6}$ alkyl, aryl, furanyl, thiophenyl, pyridyl, indolyl, quinolyl, $C_{1-6}$ alkyl-heteroaryl and $C_{1-6}$ alkyl-aryl;

$R^3$ is $S(O)_{1-2}R^9$, $SO_2N(R^7)_2$, $CO_2R^7$, $CON(R^7)_2$, $COR^7$, $CONR^{11}OR^7$ or $R^5$; $R^4$ is H or $R^5$;

$R^5$ is selected from the group consisting of $C_{1-6}$ alkyl-aryl, $C_{1-6}$ alkyl, $C_{2-6}$ alkenyl, cycloalkyl, $C_{1-6}$ alkyl-cycloalkyl, cycloalkenyl, $C_{1-6}$ alkyl-cycloalkenyl, heterocycloalkenyl, $C_{1-6}$ alkyl-heterocycloalkenyl, $C_{1-6}$ alkyl-heteroaryl, azetidinyl, pyrrolidinyl, tetrahydrofuranyl, piperidinyl, indolinyl, tetrahydroquinolinyl, $C_{1-6}$ alkyl-heterocycloalkyl, aryl, furanyl, thiophenyl, pyridyl, indolyl, and quinolyl, any of which groups is optionally substituted by a substituent selected from the group consisting of $R^6$, $C_{1-6}$ alkyl-$R^6$, aryl (optionally substituted with $R^6$), $C_{1-6}$ alkyl-aryl (optionally substituted with $R^6$), $C_{1-6}$ alkyl-heteroaryl (optionally substituted with $R^6$), furanyl (optionally substituted with $R^6$), thiophenyl (optionally substituted with $R^6$), pyridyl (optionally substituted with $R^6$), indolyl (optionally substituted with $R^6$), quinolyl (optionally substituted with $R^6$), cycloalkyl (optionally substituted with $R^6$), and azetidinyl (optionally substituted with $R^6$), pyrrolidinyl (optionally substituted with $R^6$), tetrahydrofuranyl (optionally substituted with $R^6$), piperidinyl (optionally substituted with $R^6$), indolinyl (optionally substituted with $R^6$), tetrahydroquinolinyl (optionally substituted with $R^6$), and each instance of $R^5$ may be the same or different;

$R^6$ is selected from the group consisting of halogen, CN, $NO_2$, $N(R^7)_2$, $OR^7$, $NR^7R^8$, $S(O)_{1-2}R^9$, $SO_2N(R^7)_2$, $CO_2R^{11}$, $CON(R^7)_2$, $COR^7$, $CONR^{11}OR^7$, and $C_{1-6}$ alkyl;

$R^7$ is H or a substituent selected from the group consisting of $C_{1-6}$ alkyl, aryl, $C_{1-6}$ alkyl-aryl, furanyl, thiophenyl, pyridyl, indolyl, quinolyl, $C_{1-6}$ alkyl-heteroaryl, cycloalkyl, $C_{1-6}$ alkyl-cycloalkyl, azetidinyl, pyrrolidinyl, tetrahydrofuranyl, piperidinyl, indolinyl, tetrahydroquinolinyl and $C_{1-6}$ alkyl-heterocycloalkyl, wherein said substituent is optionally substituted with a substituent selected from the group consisting of $R^9$, $COR^9$, $SO_{0-2}$, $R^9$, $CO_2R^9$, $OR^9$, SH, OH, $SCOR^9$, $CONR^{11}R^9$, $NR^{11}R^9$, halogen, CN, $SO_2NR^{11}R^9$, and $NO_2$, and for each case of $N(R^7)_2$ the $R^7$ groups are the same or different or $N(R^7)_2$ is azetidinyl, pyrrolidinyl, tetrahydrofuranyl, piperidinyl, indolinyl, tetrahydroquinolinyl optionally substituted with a substituent selected from the group consisting of $R^9$, $COR^9$, $SO_{0-2}R^9$, $CO_2R^9$, $OR^9$, SH, OH, $SCOR^9$, $CONR^{11}R^9$, $NR^{11}R^9$, CN, and $SO_2NR^{11}R^9$;

$R^8$ is selected from the group consisting of $COR^7$, $CON(R^7)_2$, $CO_2R^9$, and $SO_2R^9$;

$R^9$ is selected from the group consisting of $C_{1-6}$ alkyl, aryl, $C_{1-6}$ alkyl-aryl, furanyl, thiophenyl, pyridyl, indolyl, quinolyl, and $C_{1-6}$ alkyl-heteroaryl;

$R^{10}$ is selected from the group consisting of $OR^7$, $COR^7$, $CO_2R^{11}$, $CON(R^7)_2$, $NR^7R^8$, $S(O)_{0-2}R^9$, $SO_2N(R^7)_2$, halogen, CN, $NO_2$, and succinimidoyl (optionally substituted with $R^{11}$), phthalimidoyl (optionally substituted with $R^{11}$), hydamtionyl (optionally substituted with $R^{11}$);

and $R^{11}$ is H or $C_{1-6}$ alkyl;

and the salts, hydrates, and N-oxides.

2. The compound, according to claim 1, wherein $R^1$ is selected from the group consisting of optionally substituted $C_{1-6}$ alkyl, $C_{1-6}$ alkyl-aryl, $C_{1-6}$ alkyl-heteroaryl, and $C_{1-6}$ alkyl-heterocycloalkyl.

3. The compound, according to claim 1, wherein $R^1$ at the position adjacent to N—$R^4$ is H or alkyl.

4. The compound, according to claim 1, wherein $R^3$ is selected from the group consisting of $CO_2R^7$, $CON(R^7)_2$, $COR^7$, and $CONR^{11}OR^7$.

5. The compound, according to claim 1, wherein $R^4$ is selected from the group consisting of optionally substituted $C_{1-6}$ alkyl-aryl, $C_{1-6}$ alkyl, $C_{1-6}$ alkyl-cycloalkyl, $C_{1-6}$ alkyl-cycloalkenyl, $C_{1-6}$ alkyl-heteroaryl, azetidinyl, pyrrolidinyl, tetrahydrofuranyl, piperidinyl, indolinyl, tetrahydroquinolinyl, $C_{1-6}$ alkyl-heterocycloalkyl, aryl, and furanyl, thiophenyl, pyridyl, indolyl, quinolyl.

6. The compound, according to claim 1, wherein $R^5$ is selected from the group consisting of optionally substituted $C_{1-6}$ alkyl-aryl, $C_{1-6}$ alkyl, $C_{2-6}$ alkenyl, $C_{1-6}$ alkyl-heteroaryl, aryl, and furanyl, thiophenyl, pyridyl, indolyl, quinolyl.

7. The compound, according to claim 1, wherein $R^{10}$ is selected from the group consisting of $CON(R^7)_2$, $NR^7R^8$, $SO_2N(R^7)$ and cycloimdyl.

8. The compound, according to claim 1, selected from the group consisting of 3-benzyl-2-ethylimino-6S-(2-methylprop-1-yl)-5-oxo-tetrahydro-pyrimidine-1-carboxylic acid tert-butyl ester, 2-cyclohexylimino-6S-(2-methylprop-1-yl)-3-isopropyl-5-oxo-tetrahydropyrimidine-1-carboxylic acid tert-butyl ester, 3-(2-cyclohex-1-enylethyl)-6S-(2-methylprop-1-yl)-5-oxo-2-(1-phenylethylimino)-tetrahydropyrimidine-1-carboxylic acid tert-butyl ester, 3-cyclohexyl-6S-(2-methylprop-1-yl)-5-oxo-2-(1-phenylethylimino)-tetrahydropyrimidine-1-carboxylic acid tert-butyl ester, 6S-(2-methylprop-1-yl)-5-oxo-2-(1-phenyl-ethylimino)-3-(3-phenyl-propyl)-tetrahydro-pyrimidine-1-carboxylic acid tert-butyl ester, 3-(2-cyclohex-1-enylethyl)-2-cyclohexylimino-6S-(2-methylprop-1-yl)-5-oxo-tetrahydro-pyrimidine-1-carboxylic acid tert-butyl ester, 2-cyclohexylimino-6S-(2-methylprop-1-yl)-5-oxo-3-(2-piperidin-1-yl-ethyl)-tetrahydro-pyrimidine-1-carboxylic acid tert-butyl ester, 2-cyclohexylimino-6S-(2-methylprop-1-yl)-5-oxo-3-(3-phenyl-propyl)-tetrahydro-pyrimidine-1-carboxylic acid tert-butyl ester, 3-(2-cyclohex-1-enyl-ethyl)-6S-(2-methylprop-1-yl)-5-oxo-2-pentylimino-tetrahydro-pyrimidine-1-carboxylic acid tert-butyl ester, 6S-(2-methylprop-1-yl)-5-oxo-2-pentylimino-3-(3-phenyl-propyl)-tetrahydro-pyrimidine-1-carboxylic acid tert-butyl ester, 2-ethylimino-6S-(2-methylprop-1-yl)-5-oxo-3-(3-phenyl-propyl)-tetrahydro-pyrimidine-1-carboxylic acid tert-butyl ester, 3-(2-cyclohex-1-enyl-ethyl)-6S-(2-methylprop-1-yl)-2-(1-naphthalen-1-yl-ethylimino)-5-oxo-tetrahydro-pyrimidine-1-carboxylic acid tert-butyl ester, 6S-(2-methylprop-1-yl)-2-(1-naphthalen-1-yl-ethylimino)-5-oxo-3-(3-phenyl-propyl)-tetrahydro-pyrimidine-1-carboxylic acid tert-butyl ester, 2-allylimino-3-(2-cyclohex-1-enyl-ethyl)-6S-(2-methylprop-1-yl)-5-oxo-tetrahydro-pyrimidine-1-carboxylic acid tert-butyl ester, 2-allylimino-6S-(2-methylprop-1-yl)-5-oxo-3-(2-piperidin-1-yl-ethyl)-tetrahydro-pyrimidine-1-carboxylic acid tert-butyl ester, 2-allylimino-3-cyclohexyl-6S-(2-methylprop-1-yl)-5-oxo-tetrahydro-pyrimidine-1-carboxylic acid tert-butyl ester and 2-allylimino-6S-(2-methylprop-1-yl)-5-oxo-3-(3-phenyl-propyl)-tetrahydro-pyrimidine-1-carboxylic acid tert-butyl ester.

9. The compound, according to claim 1, in the form of a single enantiomer or diastereomer.

10. A pharmaceutical composition for use in therapy, comprising a compound of claim 1, and a pharmaceutically-acceptable diluent or carrier.

11. A method for the treatment of a condition selected from the group consisting of tumor growth, angiogenesis, tumor invasion and spread, metastases, malignant acites, malignant pleural effusion, surgical wound healing, graft-versus-host reactions, periodontitis, gingivitis, hemorrhage, corneal ulceration, and inflammation, wherein said method comprises the administration of a composition comprising a compound of claim 1.

12. A composition comprising the compound according to claim 1 and a carrier.

13. A method for reducing the activity of matrix metalloproteases comprising the administration of an effective amount of a composition according to claim 12.

* * * * *